United States Patent
Holmquist et al.

(10) Patent No.: US 11,823,797 B2
(45) Date of Patent: *Nov. 21, 2023

(54) SYSTEMS AND METHODS FOR SELF-VALIDATION OF HARDWARE AND SOFTWARE FOR SAFETY-CRITICAL MEDICAL DEVICES

(71) Applicant: Medtronic MiniMed, Inc., Northridge, CA (US)

(72) Inventors: Arnold Holmquist, Dana Point, CA (US); Eric Cohen, San Diego, CA (US); Haripriyan Hampapuram, Carlsbad, CA (US); Michael Mensinger, San Diego, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/903,181

(22) Filed: Sep. 6, 2022

(65) Prior Publication Data
US 2022/0415503 A1 Dec. 29, 2022

Related U.S. Application Data

(63) Continuation of application No. 16/865,152, filed on May 1, 2020, now Pat. No. 11,456,076.

(60) Provisional application No. 62/842,336, filed on May 2, 2019.

(51) Int. Cl.
| | | |
|---|---|---|
| *H04L 12/26* | (2006.01) | |
| *H04L 43/50* | (2022.01) | |
| *H04L 43/0811* | (2022.01) | |
| *H04W 24/08* | (2009.01) | |
| *G16H 40/67* | (2018.01) | |
| *G16H 20/17* | (2018.01) | |

(52) U.S. Cl.
CPC ............ *G16H 40/67* (2018.01); *G16H 20/17* (2018.01); *H04L 43/0811* (2013.01); *H04L 43/50* (2013.01); *H04W 24/08* (2013.01)

(58) Field of Classification Search
CPC .... H04L 43/0811; H04L 43/50; H04W 24/08; G16H 40/67; G16H 20/17
USPC ........................................................ 370/252
See application file for complete search history.

(56) References Cited

U.S. PATENT DOCUMENTS

| | | |
|---|---|---|
| 9,672,328 B2 | 6/2017 | Saint et al. |
| 9,959,391 B2 | 5/2018 | Saint et al. |
| 10,483,000 B2 | 11/2019 | Saint et al. |
| 11,456,076 B2 | 9/2022 | Holmquist et al. |
| 2006/0126846 A1 | 6/2006 | Araki |

(Continued)

*Primary Examiner* — Gbemileke J Onamuti
(74) *Attorney, Agent, or Firm* — Carter, DeLuca & Farrell LLP (57) ABSTRACT

Medical devices critical to patient health and safety that communicate with third party hardware and software, such as smart devices, require validation to ensure compatibility and correct performance. Disclosed are methods and systems to perform a self-validation of hardware and/or software components with a medical device to confirm that any combination of hardware and software are compatible and perform acceptably. If the self-validation passes then the user may safely use the system, and it may report to a cloud server that the particular configuration tested was successful. If the self-validation fails, the user will be prevented from using safety-critical aspects of the application and be notified of the incompatibility; and the results may also be reported to a cloud server.

20 Claims, 4 Drawing Sheets

(56) References Cited

U.S. PATENT DOCUMENTS

| | | |
|---|---|---|
| 2017/0068799 A1 | 3/2017 | Mensinger et al. |
| 2018/0353698 A1 | 12/2018 | Saint et al. |
| 2019/0015596 A1 | 1/2019 | Saint et al. |
| 2020/0163587 A1 | 5/2020 | Bhattacharjee |

SYSTEMS AND METHODS FOR SELF-VALIDATION OF HARDWARE AND SOFTWARE FOR SAFETY-CRITICAL MEDICAL DEVICES

CROSS-REFERENCE TO RELATED APPLICATIONS

This application is a continuation of U.S. patent application Ser. No. 16/865,152, filed on May 1, 2020, which claims the benefit of the filing date of provisional U.S. Patent Application No. 62/842,336, filed on May 2, 2019.

FIELD

The present disclosure relates to medicine administering and tracking systems, devices, and methods.

BACKGROUND

Diabetes mellitus, also referred to as diabetes, is a metabolic disease associated with high blood sugar due to insufficient production or use of insulin by the body. Diabetes is widely-spread globally, affecting hundreds of millions of people, and is among the leading causes of death globally. Diabetes has been categorized into three categories or types: type 1, type 2, and gestational diabetes. Type 1 diabetes is associated with the body's failure to produce sufficient levels of insulin for cells to uptake glucose. Type 2 diabetes is associated with insulin resistance, in which cells fail to use insulin properly. The third type of diabetes is commonly referred to as gestational diabetes, which can occur during pregnancy when a pregnant woman develops a high blood glucose level. Gestational diabetes can develop into type 2 diabetes, but often resolves after the pregnancy.

Diabetes, like other diseases and disorders, often require daily monitoring and/or treatment using medical devices that interact with portable computing and/or communication devices that a patient user may use for managing their medical condition and other purposes.

SUMMARY

Disclosed are methods, systems and devices for performing a self-validation of hardware and/or software components with a medical device to confirm that any combination of hardware and software are compatible and perform acceptably. If the self-validation passes then the user may safety use the system, and it may report to a cloud server that the particular configuration tested was successful. If the self-validation fails, the user will be prevented from using safety-critical aspects of the application and notified of the incompatibility, and the results may also be reported to a cloud server.

A medicine injection pen is one example of a medical device to which this critical device compatibility issue applies. A medicine injection device, sometimes referred to as a medicine injection "pen" or "pen device", can be used to inject a quantity of a medicine (e.g., single or multiple boluses or doses of the medicine) into a user's body, where more than one dose can be stored in a medicine cartridge contained in the pen device. "Smart pen" devices offer the benefit of simplicity over other methods of delivery, such as syringe or pump-based methods. One advantage of a smart medicine pen includes providing an automated way to track and communicate the doses dispensed by the pen in a simple, effective and reliable manner. In addition to tracking doses, some embodiments of smart pen devices in accordance with the present technology provide a dose calculator to determine the right dose to the patient user at the right time and under the right conditions. In some implementations, the smart pen device can automatically log doses in a software application ("app"), which the software application can be resident on the smart pen and/or on a companion device, like a smartphone, smartwatch, or other computing device in wireless communication with the smart pen, for example, via a wireless Bluetooth connection.

BRIEF DESCRIPTION OF THE DRAWINGS

Many advantages of the present disclosure will be apparent to those skilled in the art with a reading of this specification in conjunction with the attached drawings, wherein like reference numerals are applied to like elements and wherein.

DETAILED DESCRIPTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The intelligent medication delivery system and related methods disclosed herein boast a variety of features and components that warrant patent protection, both individually and in combination.

Medical devices critical to patient health and safety that communicate with third party hardware and software of modern computing and/or communication devices, such as smartphones, tablets, smartwatches and the like, require validation to ensure compatibility and correct performance. Typically, each configuration of the medical device is validated separately, since different hardware and software versions may behave differently. However, with these modern consumer devices, this can imply a vast number of combinations.

For example, when validating Bluetooth connectivity of a medical device with an Android OS based smartphone, aside from there being hundreds of different Android OS smartphone models from dozens of device manufacturers, each Android OS smartphone device may receive periodic operating system updates, as well as updates to the Bluetooth drivers or other connectivity drivers. This situation can lead to many thousands of possible combinations that are not practical for the medical device manufacturer to test in order to ensure proper medical device functionality and compliance with regulatory bodies, such as the Food and Drug Administration (FDA) in the United States.

Medical devices are generally critical devices to their user base, and thereby proper connectivity between the medical device and the patient user's smartphone can be paramount to the patient user's life. In comparison, errors or connectivity problems with a non-critical device (such as a wireless audio headphones or a fitness tracker) typically do not present a user risk and thus are noncritical.

In some circumstances, a total incompatibility between the medical device and the consumer device (e.g., smartphone) may result in an obvious 'symptom', such as the medical device itself or associated software application running on the smartphone failing to properly operate. Such a clear apparent incompatibility may present risks to the patient's ability to manage their medical condition, but the patient would be immediately aware of the problem to attempt to mitigate the problem. However, in some circumstances, incompatibilities between the medical device and the smartphone are not always apparent to the user and present risks to the patient user of which the patient user may be unaware.

Disclosed herein are medicine-administering systems to accurately provide health management capabilities for patients and caregivers. In one example aspect, a system includes a peripheral medical device, for example a medicine injection device (also referred to as the "pen" or "pen device"), in communication with a patient's companion device (e.g., smartphone with the appropriate system software), and a health management software application product (or "app"), in which the health management app is able to automatically validate compatibility with and connectivity to the peripheral device and the companion device. The companion device includes a software application ("app") having adaptive dose calculator and decision support modules to suggest the dose for the patient and provide control over several functionalities of the pen device.

Figure 1:
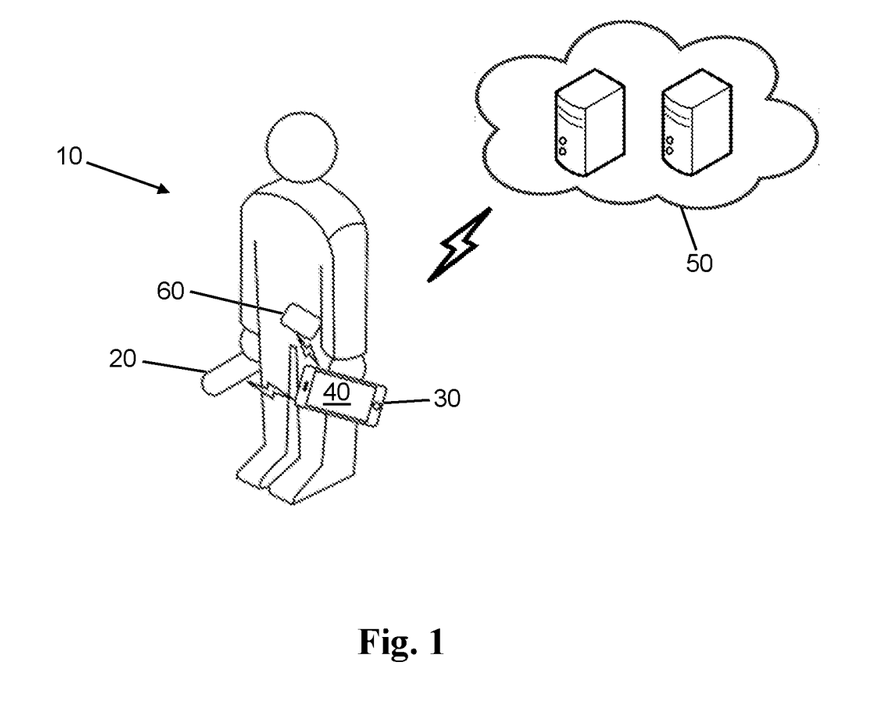
FIG. 1 is a block diagram representing an example of an intelligent medicine administering system according to one embodiment of the disclosure.

FIG. 1 shows a diagram of an example embodiment of an intelligent medicine administering system 10 in accordance with the present technology. The system 10 includes a peripheral medical device 20 (e.g. pen device 20) in wireless communication with a mobile computing and communication device 30 of a patient user, also referred to as the user's companion device. The pen device 20 is operable to select, set and/or dispense a dose of the medicine for dispensing. In some implementations, the companion device 30 includes a smart phone, tablet, and/or wearable computing device, such as a smart watch, smart glasses, etc. In some implementations, the companion device 30 is in communication with other computing devices, such as a laptop and/or desktop computer, a smart television, or network-based server computer. The pen device 20 and/or companion device 30 includes a health management app 40 that may be associated with the pen device 20 and other smart health management accessories/devices of the intelligent medicine administering system 10.

In some embodiments, the system 10 includes a data processing system 50 in communication with the companion device 30 and/or the pen device 20. The data processing system 50 can include one or more computing devices in a computer system or communication network accessible via the Internet (also referred to as "the cloud"), e.g., including servers and/or databases in the cloud.

The health management app 40 is paired with the pen device 20, which may be a prescription-only medical device. In some implementations, the pairing (also referred to as bonding) of the companion device 30 to the pen device 20 indicates to the health management application 40 that the user is ready to use all features of the application, which can augment performance and provide important features to the intelligent medicine administering system 10. Thus, in some implementations the act of pairing (bonding) enables the full functionality of the health management app 40. For example, in some cases the pairing may enable the entire app 40, in which at least a portion of the health management app 40 may be disabled without the specialized pairing; whereas in other cases, the pairing may enable certain features of the health management app 40, which otherwise provides some limited features without the specialized pairing.

In some implementations, for example, the health management app 40 can monitor and/or control functionalities of the pen device 20 and track doses (e.g. including priming doses and injection doses) dispensed by the pen device 20 and/or provide a dose calculator and/or decision support modules that can calculate and recommend a dose of the medicine for the patient user to administer using the pen device 20.

The companion device 30 can be used to obtain, process and/or display contextual data that can be used to relate to the patient user's health condition, including the condition for which the pen device 20 is used to treat. In an illustrative example, the companion device 30 is operable to track the patient user's location; the patient user's physical activity including step count, movement distance and/or intensity, estimated calories burned, and/or activity duration; and/or the patient user's interaction pattern with the companion device 30. In some implementations, the app 40 can aggregate and process the contextual data to generate decision support outputs to guide and aid the patient user in using the pen device 20 and/or managing their behavior to promote better health outcomes in treating his/her health condition.

In some embodiments, for example, the system 10 can optionally include a sensor device 60 to monitor one or more health metrics of the patient user. Examples of health metric data monitored by the sensor device 60 include analytes, such as glucose, heart rate, blood pressure, user movement, or other. In some implementations, the sensor device 60 is a wearable sensor device such as a continuous glucose monitor (CGM) to obtain transcutaneous or blood glucose measurements that are processed to produce continuous glucose values. For example, the continuous glucose monitor can include a glucose-processing module implemented on a stand-alone display device and/or implemented on the companion device 30, which processes, stores and displays the continuous glucose values for the patient user.

Figure 2:
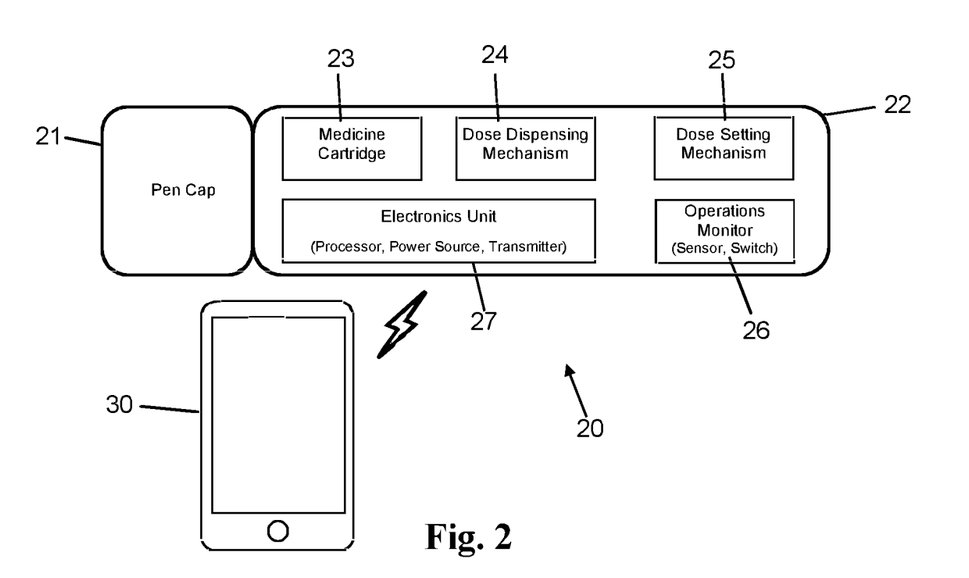
FIG. 2 is a block diagram representing an example of a pen device forming part of the intelligent medicine administering system of FIG. 1.

FIG. 2 shows a diagram of an example embodiment of the pen device 20 of the intelligent medicine administering system 10. The pen device 20 is structured to have a cap 21 configured to protect a medicine dispensing element (e.g. needle 29) and a body 22 configured to contain the medicine cartridge 23 (e.g., which can be replaceable). The pen device 20 is further structured to include a dose dispensing mechanism 24 to dispense (e.g., deliver) the medicine contained in the medicine cartridge 23 out of the pen device 20, a dose setting mechanism 25 to select and/or set the dose to be dispensed, an operations monitoring mechanism 26 to determine that the pen device 20 is being operated and/or to monitor the operation of the dose being dispensed (e.g., such as a switch and/or sensor, or an encoder), and an electronics unit 27 that can include a processor, a memory, a battery or other power source, and a transmitter. In some embodiments, for example, the pen device 20 may include a display providing a user interface that displays output data (e.g., dialed and/or dispensed dose information, the recommended dose, or other) to a user of the pen device 20. In some embodiments, the display of the pen device 20 may be a touch screen interface that can receive input data from the user.

The pen device 20 is configured in communication with the patient user's mobile computing and communication device 30, e.g., such as the user's smart phone, tablet, and/or wearable computing device, such as a smart watch, smart glasses, etc. and/or a user's laptop and/or desktop computer, a smart television, or network-based server computer.

In some implementations of the system 10, for example, to use the pen device 20, the user first dials up a dose using a dose knob. The dose knob of the pen device 20 can be included as part of the dose setting mechanism 25 and/or the dose dispensing mechanism 24. For example, the dose may be adjusted up or down prior to administration of the dose. When the user applies a force against a dose dispensing button (e.g., presses against the dose dispensing button that is caused to protrude outward from the pen's body upon dialing the dose using the dose knob), a pushing component (e.g., also referred to as a 'plunger') of the dose dispensing mechanism 24 is depressed against an abutment of the medicine cartridge 23 loaded in the pen device 20 to cause the pen device 20 to begin to dispense the medicine, in which the quantity dispensed is in accordance with that set by the dose setting mechanism 25. In such implementations, the operations monitoring mechanism 26 of the pen device 20 will begin to sense movement of a rotating component or shaft that drives the plunger, for example, in which the movement is sensed through an encoder. In some examples, the encoder can be configured to sense the rotation of a component that is coupled to the drive shaft, and as the drive shaft rotates the plunger moves linearly; and therefore, by sensing rotation of the component, the movement of the drive shaft and the plunger is sensed. Movement of the encoder may be detected as data processed by a processor of the electronics unit 27 of the pen device 10, which can be used to measure the dose. In some implementations, the processor can then store the size of the dose along with a time stamp for that dose. In some implementations, the pen device 20 can then transmit the dose and related information to the companion device 30. In such implementations when the dose is transmitted, the data associated with the particular transmitted dose is marked in the memory of the pen device 20 as transmitted. In such implementations if the dose was not yet transmitted to the companion device 30, then the data associated with the dose will be transmitted at the next time a successful communication link between the pen device 10 and the companion device 30 is established.

The operations monitoring mechanism 26 of the pen device 20 can include a sensor that can utilize any method of sensing rotary or linear movement. Non-limiting examples of such sensors include rotary and linear encoders, Hall effect and other magnetic based sensors, linearly variable displacement transducers, or any other appropriate method of sensing known in the art.

The dose dispensing mechanism 24 of the pen device 20 can include a manually powered mechanism or a motorized mechanism. In either case, a force (e.g., either produced by the patient or by an electrically-powered motor) pushes on the plunger of the dose dispensing mechanism 24 to in turn force a receiving plunger of the medicament vial or cartridge 23 to deliver the specific amount of the medicament. In some implementations, for example, the dose dispensing mechanism 24 can be adjusted to deliver the dose over a different period of time. In one example, the dose dispensing mechanism 24 can be operated such that the plunger is pushed in by an adjustable tension spring or change the speed of the motor to inject the dose over a time frame (e.g., 1 s, 5 s or other) to aid in reducing the pain of dosing. In one example, the dose dispensing mechanism 24 can be operated over a much longer period of time, e.g., to better match the dynamics of carbohydrates, which can be like an extended bolus with a pump.

The health management app 40 of the companion device 30 associated with the pen device 20 provides a user interface to allow the user to manage his/her health-related data. In some implementations, for example, the health management app 40 can be configured to control some functionalities of the pen device 20. In some implementations, for example, the health management app 40 provides an interactive user interface to allow a user to manage settings of the pen device 20, and settings for the companion device 30 (e.g., smart phone, tablet, or wearable computing device) that can affect the functionality of the system 10. In implementations, for example, the companion device 30 is an independent portable device that the user may carry on his/her person. In example embodiments of the independent portable companion device 30, the companion device 30 includes a data processing unit, wireless communication unit to allow the device to communicate with the pen device 20, and a display unit.

Figure 3:
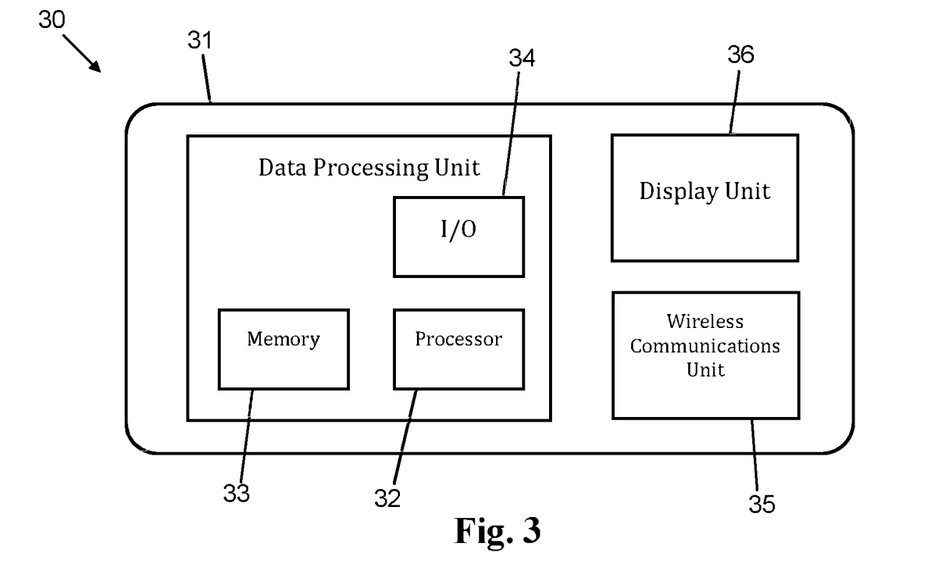
FIG. 3 is a block diagram representing an example of the companion device of the intelligent medicine administering system of FIG. 1.

FIG. 3 shows a block diagram of an example embodiment of the companion device 30 of the intelligent medicine administering system 10. The data processing unit 31 of the companion device 30 includes a processor 32 to process data, a memory unit 33 in communication with the processor 32 to store data, and an input/output unit (I/O) 34 to interface the processor 32 and/or memory 33 to other modules, units or devices of the companion device 30 or external devices. For example, the processor 32 can include a central processing unit (CPU) or a microcontroller unit (MCU). For example, the memory 33 can include and store processor-executable code, which when executed by the processor 32, configures the data processing unit 31 to perform various operations, e.g., such as receiving information, commands, and/or data, processing information and data, and transmitting or providing information/data to another device. In some implementations, the data processing unit can transmit raw or processed data to a computer system or communication network accessible via the Internet (referred to as 'the cloud') that includes one or more remote computational processing devices (e.g., servers in the cloud). To support various functions of the data processing unit, the memory 33 can store information and data, such as instructions, software, values, images, and other data processed or referenced by the processor 32. For example, various types of Random Access Memory (RAM) devices, Read Only Memory (ROM) devices, Flash Memory devices, and other suitable storage media can be used to implement storage functions of the memory unit 33. The I/O 34 of the data processing unit 31 can interface the data processing unit 31 with the wireless communications unit 35 to utilize various types of wired or wireless interfaces compatible with typical data communication standards, for example, which can be used in communications of the data processing unit 31 with other devices such as the pen device 20, via a wireless transmitter/receiver (Tx/Rx) unit, e.g., including, but not limited to, Bluetooth, Bluetooth low energy, Zigbee, IEEE 802.11, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE cellular communication methods, NFC (Near Field Communication), and parallel interfaces. The I/O 34 of the data processing unit 31 can also interface with other external interfaces, sources of data storage, and/or visual or audio display devices, etc. to retrieve and transfer data and information that can be processed by the processor 32, stored in the memory unit 33, or exhibited on an output unit of the companion device 30 or an external device. For example, a display unit 36 of the companion device 30 can be configured to be in data communication with the data processing unit 31, e.g., via the I/O 34, to provide a visual display, an audio display, and/or other sensory display that produces the user interface of the health management application 40. In some examples, the display unit 36 can include various types of screen displays, speakers, or printing interfaces, e.g., including but not limited to, light emitting diode (LED), or liquid crystal display (LCD) monitor or screen, cathode ray tube (CRT) as a visual display; audio signal transducer apparatuses as an audio display; and/or toner, liquid inkjet, solid ink, dye sublimation, inkless (e.g., such as thermal or UV) printing apparatuses, etc.

By way of example, when a dosing event occurs (e.g., an amount of fluid is dispensed from the pen device 20), a time stamp associated with the dosing event is recorded by the processing unit of the pen device 20 (e.g., stored in the memory of the pen device 20). For example, the time stamp may be the current time or a time where a count-up timer is used. When the dose information is eventually transmitted to the health management app 40 of the companion device 30, the time stamp and/or a 'time-since-dose' parameter is transmitted by the pen device 20 and received by the companion device 30 and stored in the memory 33 of the data processing unit 31 of the companion device 30. In some implementations, for example, the time of the dose can be determined without the pen device 20 having to know the current time. This can simplify operation and setup of the pen device 20. In some implementations, for example, a user time is initialized on the pen device 20 from the companion device 30, in which the user time is used for dose time tracking. Using the system 10, the health management app 40 can know the time of the dose relative to the current time.

Once the companion device 30 receives the dose related information (e.g. which can include the time information and dose setting and/or dispensing information, and other information about the pen device 20 related to the dosing event), the companion device 30 stores the dose related information in memory 33, e.g., which can include among a list of doses or dosing events. In some implementations, for example, via the user interface of the health management app 40, the companion device 30 allows the patient to browse a list of previous doses, to view an estimate of current medicament active in the patient's body ("medicament on board") based on calculations performed by a medicine calculation module 74 of the health management app 40, and/or to utilize a dose determination module 75 of the software application to assist the patient regarding dose setting information on the size of the next dose to be delivered. For example, the patient may enter carbohydrates to be eaten and current blood sugar, and the companion device 30 would already know insulin on board. Using these parameters, a suggested medicine dose (e.g., such as insulin dose), calculated by the dose determination module 75, may be determined. In some implementations, for example, the companion device 30 can also allow the patient to manually enter boluses into the pen device 20 or another medicine delivery device. This would be useful if the patient was forced to use a syringe, or if the battery in the pen device 20 was depleted.

Example embodiments and implementations of the disclosed intelligent medicine administering system 10, including the health management app 40 operable on a companion device 30 able to communicate with a medical device (e.g., medicine dispensing device such as a pen device 20), are described. Some examples of features of an intelligent medicine administering system that can be used with the example methods, devices and systems for providing a prescription-regulated software controls on the system are described in U.S. Pat. No. 9,672,328 B2, entitled "Medicine Administering System Including Injection Pen and Companion Device," the entire content of which is incorporated by reference into this disclosure for all purposes.

While the disclosed embodiments described herein are primarily based on diabetes management systems and methods involving an insulin pen, health management app associated with the insulin pen, and/or glucose monitoring devices to facilitate understanding of the underlying concepts, it is understood that the disclosed embodiments can also include treatment of other health conditions using other medications by the pen device (or an alternative peripheral medical device), health management app, and/or monitoring of other analytes by sensor devices. For example, the disclosed self-validation methods can be used in conjunction with other medical devices that would benefit from smart interaction with a health management app on a companion device.

Figure 4:
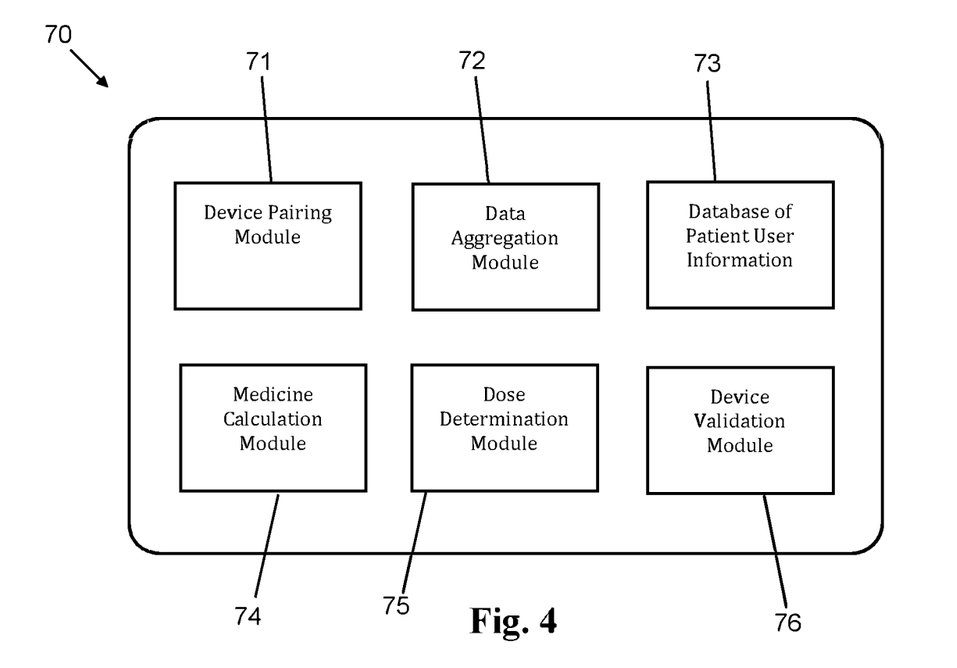
FIG. 4 is a block diagram representing an example of software architecture of data processing modules in accordance with some embodiments of the health management app of the intelligent medicine administrating system of FIG. 1.

FIG. 4 shows a block diagram of a software architecture 70 of data processing modules in accordance with some example embodiments of the health management app 40 of the intelligent medicine administrating system 10. In some embodiments, some or all of the data processing modules of the software architecture 70 of the health management app 40 are resident on the companion device 30. In some implementations of the example software architecture 70, the modules operate to control certain functionalities of the companion device 30, which includes aggregating and processing output signals transmitted by the medical injection device (e.g., pen device 20) to execute a device pairing for validation of the medicine injection device and unlocking of some or all functionality of the health management app 40 on the companion device 30.

In some embodiments of the software architecture 70, some or all of the data processing modules are resident on the companion device 30, e.g., resident in the data processing unit 31. In some embodiments of the software architecture 70 of the system 10, some of the data processing modules can be resident on the pen device 20, e.g., resident in the electronics unit 27. In some embodiments of the software architecture 70 of the system 10, some of the data processing modules may be resident on smart accessories configured for use with standard (non-intelligent) dispensing devices. Similarly, in some embodiments, for example, some of the data processing modules of the software architecture 70 can be embodied as part of a data processing system 50 in the cloud (e.g., resident on one or more cloud computers).

The data processing modules of the health management app 40 on the companion device 30 may include different or the same data processing modules of the software architecture 70 resident on the pen device 20. For example, one of the data processing modules that can be resident on and implemented by the pen device 20 includes a device pairing module 71 to receive and process the output signals from the pen device 20 to pair with the health management app 40 resident on the companion device 30.

In some implementations, the pen device 20 can be paired to the companion device 30 to enable some or all protected features of the health management app 40 associated with a specific user of the pen device 20 and/or data management on the companion device 30 which require secure access for use by the patient user. The secure pairing methods ensure that the health management app 40 resident on the companion device 30 is specifically associated with a particular pen device 20 belonging to the patient user, e.g., who may have a prescription corresponding to use of some or all features of the health management app 40.

In some embodiments of the software architecture 70 for the health management app 40, the data processing modules may also be configured to process health metric data and contextual data obtained by the health management app 40 on the companion device 30, from the pen device 20, from the sensor device 60, and/or from other devices of the patient user and/or apps on the companion device 30. In some embodiments, for example, the software architecture 70 includes a data aggregation module 72 to obtain the health metric data from a device, such as the pen device 20, a sensor device 60, and/or other devices or apps in communication with the companion device 30. The software architecture 70 includes or is in communication with a database 73 to store the health data and contextual data associated with the patient user and populations of patient users. In various embodiments, the database 73 can be resident on the data processing system 60, e.g., in the cloud. In some embodiments, the software architecture 70 includes a medicine calculation module 74 to estimate the current medicament active in the patient's body ("medicament on board" or "insulin on board" or IOB). In some embodiments, the software architecture 70 includes a dose determination module 75, such as a dose calculator module, to autonomously calculate a dose of the medicine associated with dose injections from the pen device 20 based on time-relevant and context or circumstances-relevant data specific to the patient user of the pen device 20. In some embodiments, the software architecture 70 may include a device validation module 76, configured to perform self-validation checks of compatibility and connectivity, for example compatibility of the health management app 40 and the user's companion device 30 and connectivity between the companion device 30 and the peripheral device 20 to ensure that the intelligent medicine administering system 10 is functioning properly. The example modules shown in the software architecture diagram can be organized to provide data to one another in various ways, including directly (e.g., module-to-module) and/or indirectly (e.g., via an intermediary module), based on a periodic, an intermittent, and/or a per-request basis.

Figure 5:
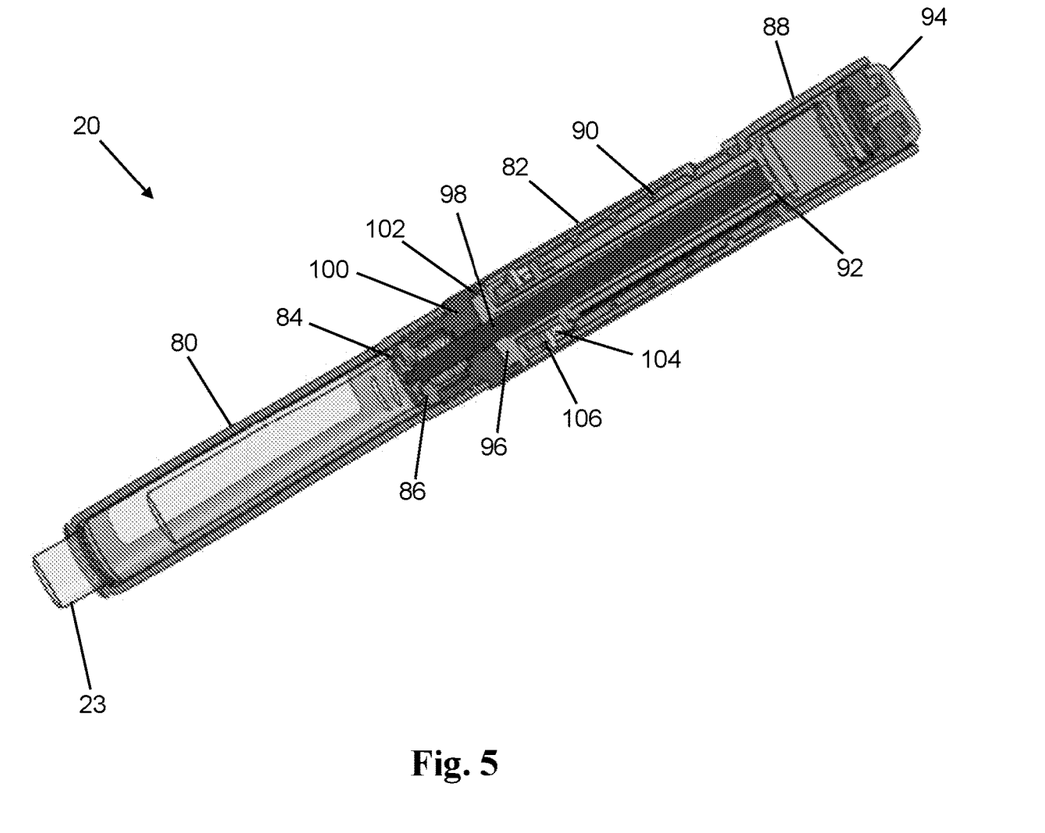
FIG. 5 is a schematic illustration of an example embodiment of the pen device shown in FIG. 2.

FIG. 5 shows a schematic illustration of an example embodiment of the pen device 20. The example shown in FIG. 5 illustrates the structural arrangement and interaction of the example modular units and mechanisms depicted in FIG. 2 for various operations of the pen device 20. As shown in FIG. 5, the pen device 20 of the present example includes a mechanism to actuate a force to cause a displacement of a piston, which resides within a medicament vial or cartridge 23. By way of example, displacement of the piston of the medicament vial 23 forces a volume of the medicament (that is proportional to the displacement of the piston) out of the vial 23, e.g., allowing the medicament to be injected into a patient. The vial 23 is held within a medicament housing 80 of the pen device 20. The medicament housing 80 is attached to a main body housing 82 of the pen device 20, which includes a dose setting and dispensing mechanism and electronics unit of the pen device 20. In some embodiments, for example, the medicament housing 80 and the main body housing 82 may be a singular housing structure. The medicament housing 80 may be structured to include a chamber to hold and/or encase the medicament vial 23 within the housing 80. The pen device 20 may also include a detachable pen cap (not shown) to cover an end of the pen device 20 that exposes a needle assembly (not shown) to disburse the medicine out of the pen device 20 when dispensed from the vial 23. The pen device 20 may include a vial spring 84 that provides a force on a screw retractor 86 to push the medicament vial 23 into the medicament housing 80 to ensure dose accuracy. The pen device 20 includes a dose knob 88 attached to or included as part of the housing 82, where the dose knob 88 is coupled to the housing 82 by a non-self-locking thread 90. In some embodiments, for example, an electronics housing 92 may reside within the dose knob 88, in which the electronics housing 92 contains the electronics unit 27 of the pen device 20. In some embodiments, the dose setting mechanism 25 includes the dose knob 88. When the dose knob 88 is rotated into or out of the housing 82 to adjust the dose, the electronics housing 92 does not turn. However, when translational or axial force is placed to the dose button 94 (e.g., in which resides the electronics housing), a catch structure component is engaged to lock the electronics housing 92 and dose knob 88 together, forcing them to rotate together as the pair travel distally into the housing 82 upon actuation of the dose dispensing mechanism to apply force to the dose knob 88 to cause dispensing of the set dose. The rotation of the dose knob 88, e.g., which can be via the electronics housing 92, rotates a shaft 96 (e.g., which can be configured as a bi-directional clutch shaft). The shaft 96 in turn rotates a dose screw 98, which rides within a nut 100 that is fixed to the housing 82. This rotation causes the dose screw 98 to extend out of the housing 82 causing an injection of medicament. In some embodiments, for example, the dose dispensing mechanism can include a friction-causing structure 102, e.g., which can be coupled to the exemplary bi-directional clutch shaft 96 to present a friction surface (i.e., a surface that provides friction) to make contact with the nut 100 or housing body 82 or other internal structure of the dose dispensing mechanism. The friction surface acts from the bi-directional clutch shaft 96 to the housing 82 or nut 100 to prevent rotation of the shaft 96 while the dose setting mechanism is being adjusted via turning of the dose knob 88, while also allowing the friction to be overcome during the dose dispensing operation. In addition, by overcoming friction in the opposite direction, the dose screw 98 may be driven back into the housing 82 and prepared for a new cartridge of medicament to be loaded. In some embodiments, for example, the pen device 20 includes a screw retractor component 86 that is axially fixed to the housing but rotationally free. The screw retractor component 86 is operable to be bent in to "grab" the non-circular cross section of the dose screw 98 allowing it to be rotated relative to the housing 82 and driven back into the housing 82. In some implementations, for example, the various components of the pen device 20 may be manufactured by injection molding, machining or another similar process. In embodiments including the bi-directional clutch shaft 96, for example, the pen device 20 is capable of allowing retraction of the lead screw, and repeatability of operation of the dose dispensing mechanism.

In some embodiments, the sensor unit of the pen device 20 includes a rotational encoder, for example, between the dose knob 88 (e.g., which can be coupled to the jack screw) and the housing 82, and in electrical communication with the electronics unit 27 contained in the electronics housing 92. The encoder is included in a sensor unit to determine the quantity of the dose set by the dose setting mechanism, and/or, the quantity of the dose dispensed by the dose dispensing mechanism. In some implementations, for example, the encoder may be configured in the pen device 20 to determine the dispensed dose by detecting rotation of the lead screw which is correlated with displacement of the pusher foot which is correlated with displacement of the receiving plunger in the vial 23, which in turn is correlated with dispensed insulin. In some embodiments, for example, the encoder may include two flat plates with contacts in between them. The plates may be aligned perpendicular to a longitudinal axis of the device. For one plate, a contact plate 104 is rotationally fixed to the jack screw, e.g., which can be via the electronics housing 92; and for the other plate, a code wheel 106 is rotationally fixed to the housing 82. In some implementations, for example, when relative motion occurs between these two plates during dosing, the relative motion is measured and transmitted to the data processing and communications unit for processing, storage and/or transmission to the companion device 30.

In some embodiments of the pen device 20, for example, the dose setting and dispensing mechanism may include a mechanism in which the dose screw 98 is comprised of an elongate nut which screws in and out of the housing to provide dosing. The nut component in the previous described embodiment (e.g., nut 100) may include a separate screw structure; whereas in this embodiment of the dose screw, the nut component is part of the dose screw including exterior threads and is coupled to the housing 82. When the exemplary bi-directional clutch shaft 96 provides rotation, it operates on the jack screw, e.g., in which the dosing nut in this case threading it out of the housing.

Example Method for Self-Validating Hardware and Software

As technology and treatment improve over time, many medical patients are able to manage their medical issues and/or treatments through the use of personal peripheral medical devices in combination with a corresponding software application installed on their companion device (e.g. smartphone, tablet, smart watch, or other portable communications device.) By way of example, the personal peripheral medical devices may be treatment-administering devices configured to administer a therapeutic dose of medicine to the patient (e.g. pen device 20), monitoring devices configured to monitor, record, and/or analyze patient physiological information (e.g. sensor device 60), or devices having a combination of treatment and monitoring features. A serious, unmitigated risk for some of these patients (e.g. diabetes patients) is the risk of poor or intermittent connectivity of a safety-critical peripheral device, such as a Bluetooth-enabled insulin-dispensing pen device 20 with a corresponding health management app 40 installable on the patient user's companion device 30 that calculates (among other things and by way of example) insulin doses to be taken. In these cases, the hardware and software may function well enough to intermittently communicate and appear to be working, but may not be able to connect and display current data properly. For example, if a connectivity problem causes the app 40 to not have current dose information from the pen device 20, then the app 40 may direct a patient user to take too much insulin or to re-administer a dose that was already taken.

Instead of pre-validating every possible combination of hardware and software, the disclosed intelligent medicine administering system 10 may perform a self-validation upon initial setup and/or at regular intervals to confirm that the user's combination of hardware (e.g., pen device 20 and companion device 30) and software (e.g. health management app 40 and companion device operating system or "OS") are compatible and perform acceptably. If the self-validation passes, then the system 10 may indicate such so that the user knows he/she may safely use the system (and the system 10 may optionally report to a system server (e.g., cloud server 50) that the particular configuration tested was successful). On the other hand, if the self-validation fails, then the system 10 may prevent the patient user from using safety-critical aspects of the health management application 40 and will be notified of the incompatibility (and the system 10 may optionally report the failure results to the cloud server 50). In this way, the particular hardware device (e.g., companion device 30) or particular software configuration of the companion device 30 may be "black-listed" so that the device manufacturer and/or user community would know that this device/software configuration is incompatible with the medical device (e.g., pen device 20 and/or health management app 40); and as a result, for example, the manufacturer may promptly research updates or corrections to enable compatibility with this configuration. White-listing or black-listing may also allow future users to safely use or be notified of incompatibility without needing to perform the self-validation, e.g., prior to purchasing a particular companion device 30 or installing the health management app 40.

In various embodiments, the health management app 40 associated with the medical device (e.g., pen device 20) can be pre-validated to run on a specific Operating System (OS) version on the user companion device 30 having at least a minimum display resolution and color capabilities. Prior to allowing the user to install and/or run the health management app 40, the device minimum requirements may be verified. Alternatively, or in addition to verification before installation, the app 40 may verify that the companion device 30 has the minimum system requirements (e.g. OS version and display resolution and color capabilities).

In various embodiments, the user's peripheral medical device may require a specific hardware interface and/or software library that is available on the user's companion device 30, such as Bluetooth, Bluetooth Low Energy (BLE), Wi-Fi, or other. The health management app 40 may verify the presence and/or version of drivers or firmware for these peripherals directly. If the app 40 determines that the companion device 30 meets the minimum system requirements, the app 40 then must verify acceptable connectivity with the peripheral medical device (e.g. pen device 20).

In some embodiments, to execute the verification process, the peripheral medical device 20 and the companion device 30 (e.g. having the health management app 40 thereon) must be within a wireless electronic communication range of one another and activated (e.g. powered on). If the app 40 is unable to locate (e.g. via Bluetooth or other wireless communication technology) the peripheral device 20 upon initiation of the device validation module 76, then the app 40 may alert or instruct the user (e.g. via audio indication and/or visual instruction displayed on the display unit 36 of the companion device 30) to bring the peripheral medical device 20 within wireless electronic communication range of the user's companion device 30 and/or activate the peripheral device 20 if necessary. The app 40 may then proceed with the verification process, which by way of example may include verifying one or more of connection latency (e.g., the amount of time needed to transfer data between the peripheral device 20 and the companion device 30), connection bandwidth (e.g. amount of data transferred in a given amount of time), and integrity of data transferred.

By way of example, upon receipt of instructions from the health management app 40 to initiate verification of connection latency, the peripheral medical device 20 begins advertising for connection (e.g. via Bluetooth or other suitable wireless communication technology) and initiates a timer. Upon successful connection, the peripheral medical device 20 transmits the timer value to the health management app 40, indicating the latency from initial advertising to successful connection. Latency time must be below a predetermined threshold value to indicate a successful verification.

By way of example, upon receipt of instructions from the health management app 40 to initiate verification of connection bandwidth, the peripheral device 20 transmits a predetermined sequence of data or data packets to the app 40 over a predetermined amount of time. Alternatively, for example, the peripheral device 20 may transmit a predetermined amount of data, and the total transfer time is measured by the peripheral device 20 and/or the app 40, possibly timing out if a maximum threshold time value is exceeded. Bandwidth rate of data per time must be above a predetermined threshold to indicate a successful verification.

By way of example, upon receipt of instructions from the health management app 40 to initiate verification of integrity of data transferred, the peripheral device 20 transmits a predetermined sequence of data or data packets (which may be the same data transmitted to verify connection bandwidth) to the health management app 40, and the app 40 compares the received data to a known predetermined sequence of expected data. By way of example, in some implementations the data may be factory-set data, or data calculated from a factory-set algorithm, resident on the peripheral device 20 and sent to the companion device 30 where the health management app 40 compares the sequences (received and expected). In some implementations, the data sequence may be established at the time of connection by the app 40 sending the peripheral device 20 a data sequence or value from which to calculate a data sequence, which the peripheral device 20 receives and then retransmits to the companion device 30 where the app 40 compares the received data sequence to the sent data sequence. The data sequence received by the app 40 must match the expected data sequence to indicate a successful verification.

If the health management app 40 determines that the companion device 30 meets the minimum system requirements (e.g. OS version, display resolution and color capabilities, hardware interface, software library), one or more connectivity tests (e.g. latency, bandwidth, and data integrity tests) are successful, and there are no other fatal errors (e.g., such as failing to connect or failing to run the app 40 at all), then the health management app 40 may determine the configuration to be validated and acceptable, and the system 10 is unlocked for the user to use. If any portion the connectivity check fails, the health management app 40 may consider the hardware/software configuration of the companion device 30 to be unacceptable and the system 10 is locked, preventing use by the user (e.g. of at least some of the features of the health management app 40). By way of example, in some embodiments, in the case of a failed verification, the health management app 40 may present a popup notification on the display unit 36 of the companion device 30 informing the user of the failed connectivity verification and possible fixes, for example by prompting the user to update to the latest system software.

It should be noted that the connection latency test, connection bandwidth test, and integrity of data sent test are described herein by way of example, and other connectivity verification tests may be utilized by the health management app 40 to verify connectivity between the companion device 30 and the peripheral device 20 without departing from the scope of this disclosure. By way of example, in some implementations, at least one connectivity test must be satisfied for the health management app 40 to verify connectivity and unlock the system 10. In some implementations, all connectivity tests provided by the health management app 40 must be satisfied for the health management app 40 to verify connectivity and unlock the system 10.

Optionally, in some embodiments, portions of the system 10 or health management app 40 may be enabled for the user regardless of validated status, and only safety-critical portions of the system 10 or app 40 may be enabled or disabled based on validation results.

Occasionally, in some embodiments, one or more of the validation tests may fail due to external factors, e.g., such as a peripheral device 30 out of range of the companion device 30, or incorrect user inputs that do not indicate an unsuccessful configuration. Because of this possibility, the health management app 40 may repeat the validation sequence multiple times to allow passing on a subsequent attempt.

Figure 6:
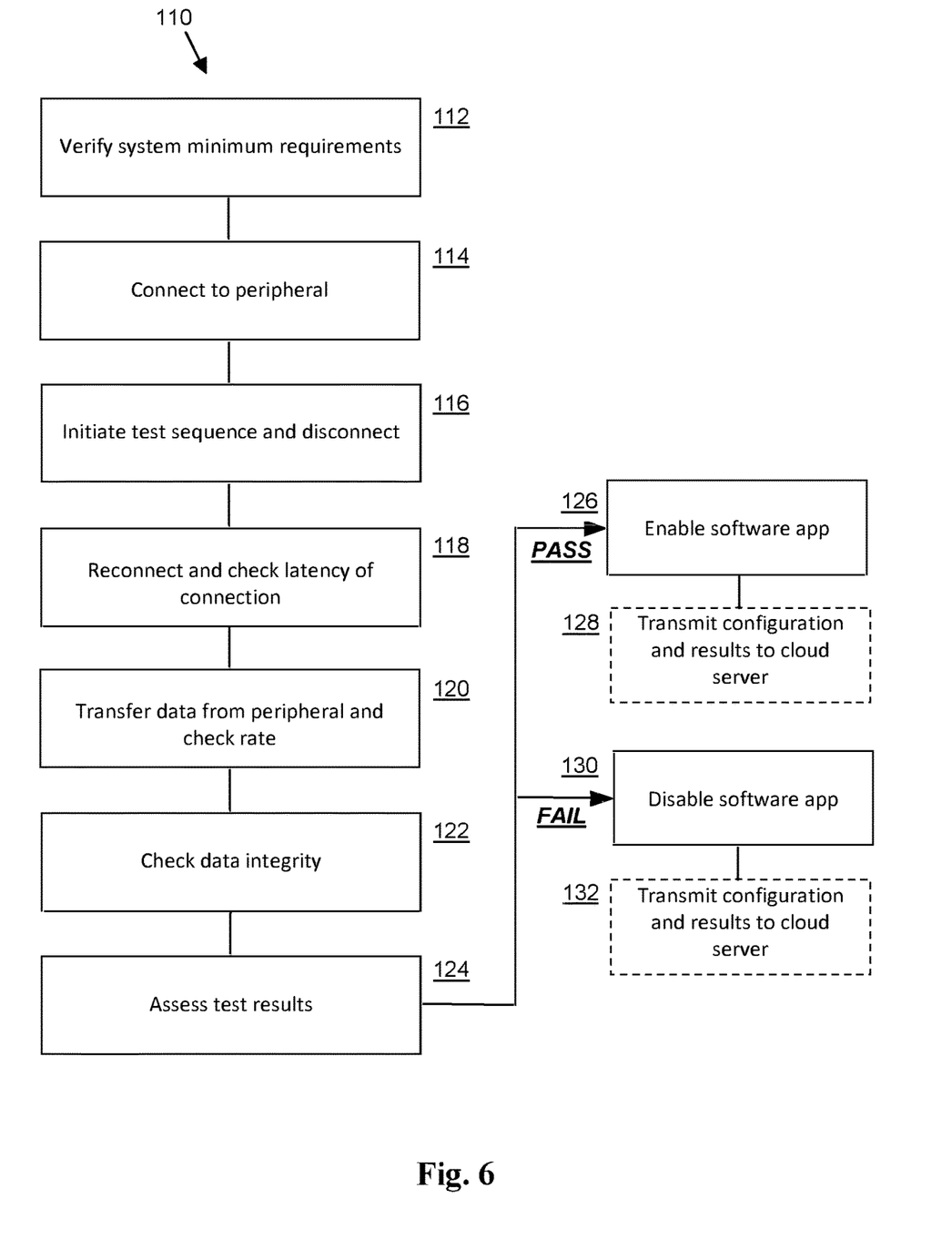
FIG. 6 is a diagram of an example embodiment for a critical device self-validation method in accordance with the present technology.

FIG. 6 shows a process flow diagram of an example embodiment for a critical device self-validation method 110 in accordance with the present technology. By way of example, in some implementations, the method 110 can be used for a peripheral medical device 20 comprising a Bluetooth Low Energy (BLE) Insulin Pen that connects to a health management app 40 running on a user's companion device 30 comprising an Android smart phone. The app 40 may be pre-validated to run properly on a given Operating System stack version (e.g., API version) and on companion devices 30 with minimum screen display properties (e.g., resolution and color capabilities) and containing a BLE chipset. By way of example, the app 40 upon installation may be partially disabled, with safety-critical features such as display of insulin doses and dose calculations disabled to the user.

By way of example, the method 110 includes a process 112 to verify the system minimum requirements of the user device (e.g., companion device 30, which can be embodied on a smartphone). In some implementations of the process 112, for example, the app 40 may verify the Operating System version, display properties, and presence of a wireless transceiver module (e.g., BLE chipset) of the companion device 30.

The method further includes a process 114 to connect to a peripheral device 20, i.e., the medical device (e.g., pen device 20). In some implementations of the process 114, the health management app 40 prompts the user to initiate bonding to a new pen device 20, and the app 40 prompts the user to activate the pen device 20 in the vicinity (e.g., within wireless electronic communication range) of the companion device 30 (e.g., smartphone). In such implementations, necessary secure bonding sequences may be included, such as the bonding sequences enabled by the device pairing module 71 described above.

The method 110 further includes a process 116 to initiate the test sequence and disconnect. In some implementations of the process 116, the health management app 40 commands the newly connected pen device 20 to conduct the connectivity test sequence, and the BLE connection is terminated.

The method further includes a process 118 to reconnect and check latency of the connection. In some implementations of the process 118, the pen device 20 (via the app 40) initiates a connection by advertising via a wireless protocol (e.g., BLE). For example, the pen device 20 may start a timer at the beginning of advertising and reports the elapsed time upon successful connection to the companion device 30 (e.g., smartphone). The app 40 confirms whether the latency value is below a set threshold, e.g., 3 seconds, 10 seconds, 30 seconds, or another predetermined threshold.

The method further includes a process 120 to transfer data from the peripheral device 20 and check the rate of data transfer. In some implementations of the process 120, the pen device 20 can now transmit a pre-set sequence of data packets for a pre-set amount of time. Upon completion of the time window, the app 40 verifies that a minimum number of packets were received, e.g., 10 packets, 20 packets, or 100 packets, or another amount of packets.

The method further includes process 122 to check data integrity. Since the data transmitted during the test was predetermined, in some implementations of the process 122, the app 40 is able to verify that the data received by the companion device 30 correctly matches an expected pre-set sequence. For example, if the received data is correct or has an acceptable degree of error when compared to the expected data, then the app 40 may consider the data integrity as acceptable.

The method further includes a process 124 to assess the test results. In some implementations of the process 124, if tests of the previous processes were successful, then this indicates that the app 40 is not only compatible with the companion device 30, but will perform with reliable connectivity with the peripheral device 20 in this configuration as the system 10, e.g., including the BLE insulin pen peripheral device 20, smartphone companion device 30, and health management app 40.

When the test is assessed as successful, the process 124 can output a "PASS" to direct the method 110 to implement a process 126 to enable all features of the software application 40; whereas when the test is assessed as a failure, the process 124 can output a "FAIL" to direct the method 110 to implement a process 130 to disable the software application. In some implementations of the process 126, the display of insulin data and dose calculations are enabled only if the test was successful.

In some embodiments of the method 110, the method 110 includes a process 128 (or 132) to transmit configuration and results to a system server 50. In some implementations, the system configuration details and result of the connectivity validation test are reported to cloud servers 50, enabling a central repository of acceptable and unacceptable configurations tested in the field.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them.

Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

It is intended that the specification, together with the drawings, be considered exemplary only, where exemplary means an example. As used herein, the singular forms "a", "an" and "the" are intended to include the plural forms as well, unless the context clearly indicates otherwise. Additionally, the use of "or" is intended to include "and/or", unless the context clearly indicates otherwise.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A medicine administering system, comprising:
   a medical device configured for administering medicine; and
   a software application configured to be installed on a mobile communication device, the software application including instructions for:
      establishing a wireless communication connection between the medical device and the mobile communication device;
      terminating the established wireless connection between the medical device and the mobile communication device; and
      executing a connectivity test, the connectivity test including:
         reestablishing the wireless connection between the medical device and the mobile communication device;
         causing data to be transferred from the medical device to the mobile communication device via the reestablished wireless connection between the medical device and the mobile communication device; and
         determining an integrity of the transferred data.

2. The medicine administering system according to claim 1, wherein the connectivity test further includes determining a transfer rate of the transferred data.

3. The medicine administering system according to claim 1, wherein the connectivity test further includes determining a latency of the reestablished wireless connection between the medical device and the mobile communication device.

4. The medicine administering system according to claim 3, wherein the latency of the reestablished wireless connection between the medical device and the mobile communication device is determined based on an elapsed period of time between an initiation of an advertising of data by the medical device and the reestablishing of the wireless connection between the medical device and the mobile communication device.

5. The medicine administering system according to claim 1, wherein the data caused to be transferred from the medical device to the mobile communication device via the reestablished wireless connection between the medical device and the mobile communication device is a pre-set sequence of data packets.

6. The medicine administering system according to claim 5, wherein the connectivity test further includes determining the integrity of the transferred data based on a comparison between the pre-set sequence of data packets and an expected pre-set sequence of data packets.

7. The medicine administering system according to claim 5, wherein the connectivity test further includes verifying that a minimum number of the pre-set data packets were received by the mobile communication device.

8. The medicine administering system according to claim 1, wherein the connectivity test further includes assessing a result of the connectivity test.

9. The medicine administering system according to claim 1, wherein the software application includes instructions for verifying a system minimum requirement of the mobile communication device.

10. The medicine administering system according to claim 1, wherein establishing a wireless communication connection between the medical device and the mobile communication device includes generating a prompt on the mobile communication device for a user to activate the medical device within a wireless communication range of the mobile communication device.

11. A medicine administering system, comprising:
    a medical device configured for administering medicine; and
    a software application configured to be installed on a mobile communication device, the software application including instructions for:
       establishing a wireless connection between the medical device and the mobile communication device;
       terminating the established wireless connection between the medical device and the mobile communication device;
       commanding the medical device to conduct a connectivity test, the connectivity test including:
          reestablishing the wireless connection between the medical device and the mobile communication device;
          determining a latency of the reestablished wireless connection between the medical device and the mobile communication device; and
          causing data to be transferred from the medical device to the mobile communication device via the reestablished wireless connection between the medical device and the mobile communication device.

12. The medicine administering system according to claim 11, wherein the connectivity test further includes determining an integrity of the data transferred from the medical device to the mobile communication device via the reestablished wireless connection.

13. The medicine administering system according to claim 12, wherein the integrity of the data transferred from the medical device to the mobile communication device is determined based on a comparison between a pre-set sequence of data packets transferred from the medical device to the mobile communication device and an expected pre-set sequence of data packets.

14. The medicine administering system according to claim 11, wherein the connectivity test further includes assessing a result of the connectivity test.

15. The medicine administering system according to claim 11, wherein the software application includes instructions for verifying a system minimum requirement of the mobile communication device.

16. A medicine administering device configured for pairing with a mobile communication device, comprising:
   an electronics unit including a processor and a memory storing instructions, which when executed by the processor, cause the electronics unit to:
      establish a wireless connection between the medicine administering device and the mobile communication device;
      terminate the established wireless connection between the medicine administering device and the mobile communication device; and
      execute a connectivity test by:
         reestablishing the wireless connection between the medicine administering device and the mobile communication device; and
         transferring data from the medicine administering device to the mobile communication device via the reestablished wireless connection for determining a transfer rate of the transferred data and an integrity of the transferred data.

17. The medicine administering device according to claim 16, wherein the instructions, when executed by the processor, cause the electronics unit to transmit, to the mobile communication device, an elapsed period of time between an initiation of an advertising of data by the medical device and the reestablishing of the wireless connection between the medicine administering device and the mobile communication device for determining a latency of the reestablished connection.

18. The medicine administering device according to claim 16, wherein the data transferred from the medicine administering device to the mobile communication device via the reestablished wireless connection is a pre-set sequence of data packets.

19. The medicine administering device according to claim 18, wherein the integrity of the transferred data is determined based on a comparison between the pre-set sequence of data packets and an expected pre-set sequence of data packets.

20. The medicine administering device according to claim 18, wherein the pre-set sequence of data packets is transferred from the medicine administering device to the mobile communication device for a pre-set amount of time for verifying that a minimum number of the pre-set data packets were received by the mobile communication device.

* * * * *